US00PP08389P

United States Patent [19]

DeCoster

[11] Patent Number: Plant 8,389

[45] Date of Patent: Sep. 21, 1993

[54] SPATHIPHYLLUM PLANT NAMED EMERALD SWIRL

[75] Inventor: Paul DeCoster, Melle, Belgium

[73] Assignee: Cari-Mar International, Inc., Miami, Fla.

[21] Appl. No.: 840,187

[22] Filed: Feb. 24, 1992

[51] Int. Cl.[5] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

A new and distinct Spathiphyllum plant named Emerald Swirl, characterized by its dark green glossy, thick and leathery leaves, numerous large flowers held closely above the foliage on strong pedicels, with the flowering habit resulting in substantially less cubic feet being required for shipping, and by the distinctive twist or swirl at the upper or outer ends of the leaves and flowers.

2 Drawing Sheets

The present invention comprises a new and distinct cultivar of Spathiphyllum, botanically known as Spathiphyllum and referred to by the cultivar name Emerald Swirl.

The new cultivar is a product of a planned breeding program, and was originated from a cross made by the inventor Paul DeCoster in Melle, Belgium.

The female, or seed pollen parent was Tasson, and the male, or pollen parent was Petite.

Emerald Swirl was discovered and selected as a flowering plant within the progeny of the stated cross by the inventor in a controlled environment in Melle, Belgium, and identified as seedling No. 7. Subsequent asexual reproduction by tissue culture has demonstrated that the combination of characteristics as herein disclosed for the new cultivar are firmly fixed and are retained through successive generations of asexual reproduction.

The following traits has been repeatedly observed and in combination distinguish Emerald Swirl as a new and distinct cultivar:

1. Very dark green glossy leaves which maintain their green color.
2. Numerous large flowers held closely above (approximately 15-25 cm) the foliage on strong pedicels.
3. Leaves are thick and leathery with heavy veination.
4. Both the flowers and the leaves have a distinctive twist or swirl at their upper or outer ends.

BRIEF DESCRIPTION OF THE VARIOUS VIEWS OF THE DRAWING

In the color photographic drawings, on the first sheet of the drawing, the photo at the top is a front perspective view of a typical specimen of 'Emerald Swirl'. The lower photograph comprises an enlarged showing of a typical leaf of 'Emerald Swirl'. The photo of the second sheet is an enlarged showing of the flower parts of the plant. The number "7" appearing in the drawing refers to the seedling number given to the new variety, as above noted.

BOTANICAL DESCRIPTION

The following observations, measurements and values describe plants grown in Homestead, Fla. under greenhouse conditions which closely approximate those generally used in horticultural practice. Color references are made to the Royal Horticultural Society (R.H.S.) Colour Chart, except where general color terms of ordinary significance are used. The color values were determined between 10:00-12:00 a.m. on Jun. 13, 1991 under 100 foot candles of artificial light at Homestead, Fla.

The new cultivar can be compared to the well known cultivar Viscount and the female parent Tasson. Similarities between all three cultivars are medium plant size and glossy leaves. Emerald Swirl is distinguished from both cultivars by its thicker and more leathery dark green leaves carried on stiff petioles, and its longer flowers which are carried on thicker stems.

Classification:

*Botanical.*—Spathiphyllum cv. Emerald Swirl.

*Commercial.*—Spathiphyllum.

Parentage:

*Male parent.*—Petite.

*Female parent.*—Tasson.

Propagation: By tissue culture.

Plant: From 40 cm to 51 cm tall (above soil level) when grown in 25 cm pots, and approximately 89 cm in diameter when fully grown.

*Growth Habit.*—Medium size, well branched, full.

Leaves:

*Form and Size.*—Simple, ovate with acuminate apices and obtuse base. Apices typically curled. Leaf blade entire. Leaf blade width is slightly asymmetrical with respect to midvein. 24 to 28 cm in length and 15-17.5 cm in width.

*Texture.*—Smooth, thick, leathery, glossy or polished.

*Veins.*—Sunken, midvein prominent.

*Color.*—Upper Surface: Yellow-green 147A. Lower Surface: Green 137A.

Flowers:

*Buds.*—Spathe tightly rolled around spadix and extrudes from petiole sheath. Spathe is fully opened when pedicel is fully elongated approximately 50 cm to 60 cm above soil level.

Spathe:

*Size.*—9.5 cm to 13.5 cm wide by 16 cm to 23 cm long.

*Color (RHS).*—White 155C.

*Arrangement.*—Single flower on straight, upright pedicel.

*Shape.*—Ovate with curled acuminate apices, obtuse base narrowly decurrent on pedunole.

*Flowering.*—Flowers naturally in 8-10 months from tissue culture. Seasonally free flowering in November through June, and can be forced to flower at other times with Giberillic acid.

Spadix:

*Size.*—6.5 cm to 10.5 cm long.

*Color (RHS).*—Yellow — green 150D.

*Longevity.*—Flowers remain white for approximately 45 days and slowly regress to a green color.

*Other characteristics.*—Held above foliage 10 cm to 20 cm on strong pedicels.

Reproductive organs:

*Anthers and filaments.*—Not clearly visible.

*Pistils.*—Protruding between staminate flowers, firmly fixed to main axil.

Roots: Fleshy main roots with fine lateral roots.

Disease Resistance: Resistant to phytophthora.

I claim:

1. A new and distinct cultivar of Spathiphyllum plant named Emerald Swirl, as illustrated and described.

* * * * *

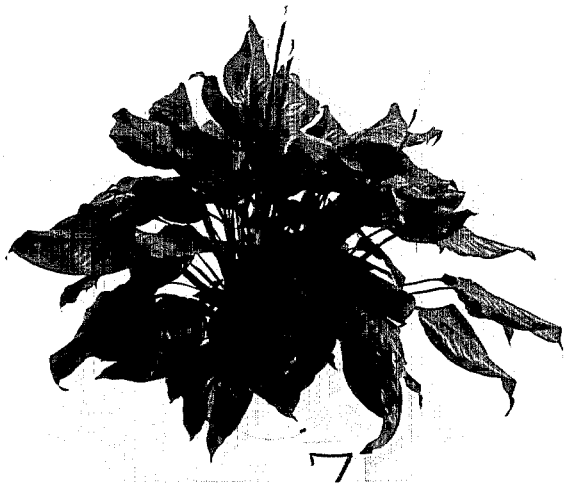
7
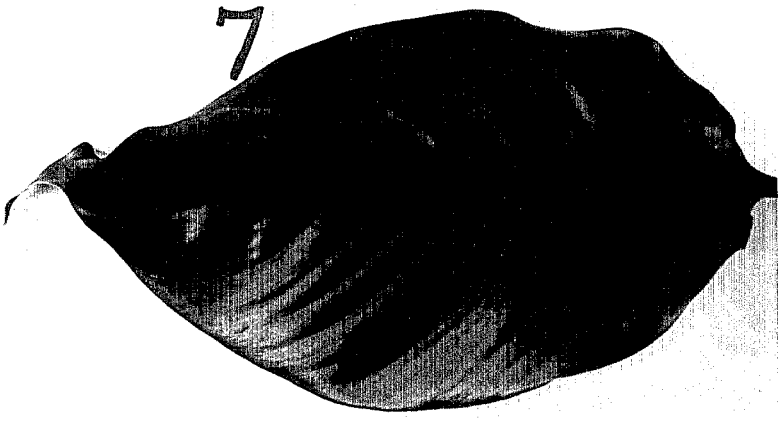
7

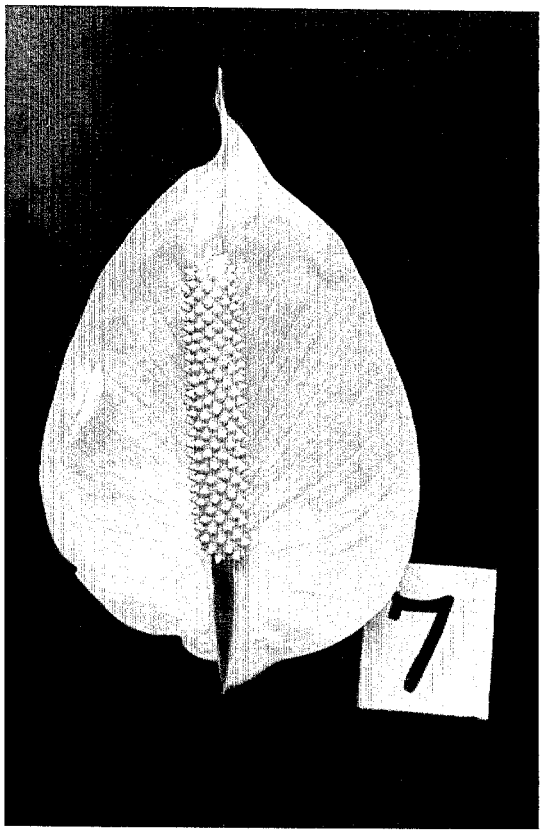
7